United States Patent [19]

Grace et al.

[11] Patent Number: 4,911,892
[45] Date of Patent: Mar. 27, 1990

[54] APPARATUS FOR SIMULTANEOUS DETECTION OF TARGET GASES

[75] Inventors: Richard Grace; Alberto M. Guzman; Marc A. Portnoff; Paul D. Runco; Lymperios N. Yannopoulos, all of Pittsburgh, Pa.

[73] Assignee: American Intell-Sensors Corporation, Pittsburgh, Pa.

[21] Appl. No.: 17,838

[22] Filed: Feb. 24, 1987

[51] Int. Cl.⁴ .............................................. G01N 31/12
[52] U.S. Cl. .......................................... 422/94; 73/23; 338/34; 422/90; 422/95; 422/98; 340/634
[58] Field of Search ........................ 422/90, 94, 95, 98; 73/23; 338/34; 340/634

[56] References Cited

U.S. PATENT DOCUMENTS

| | | | |
|---|---|---|---|
| 3,970,431 | 7/1976 | Wise | 338/34 |
| 4,347,732 | 9/1982 | Leary | 338/34 |
| 4,457,161 | 7/1984 | Iwanaga et al. | 340/634 |
| 4,542,640 | 9/1985 | Clifford | 73/23 |

Primary Examiner—Barry S. Richman
Assistant Examiner—Timothy M. McMahon
Attorney, Agent, or Firm—Buchanan Ingersoll

[57] ABSTRACT

A gas sensing thick film is positioned on an insulating substrate in contact with a pair of electrodes. A nonporous glass layer surrounds the film to stabilize it on the substrate. A heating element maintains the film at a preselected elevated temperature. The gas sensing thick film has a response characteristic for a preselected target gas to be detected which is enhanced by impregnating the film with platinum or palladium chlorine free compounds. The response characteristic of the gas sensing film is further increased by promoting combustion of interference gases on an outer filter layer fabricated of either conductive or nonconductive material. The incorporation of an insulating material between the gas sensing film and the outer filter layer also serves to increase the relative response of the gas sensing film to a preselected target gas.

23 Claims, 4 Drawing Sheets

APPARATUS FOR SIMULTANEOUS DETECTION OF TARGET GASES

BACKGROUND OF THE INVENTION

1. Field of the Invention

This invention relates to combustible gas sensors and more particularly to catalytically activated gas sensors having a multi-layered metal oxide film structure for improving the selective detection of target gases.

2. Description of the Prior Art

U.S. Pat. No. 4,542,640 discloses a selective gas detection system in which semiconductor gas sensors are used to detect polluting, toxic, and combustible gases such as carbon monoxide, methane, hydrogen sulfide, hydrocarbons, and many other combustible vapors commonly found in ambient air. These target gases occur as impurities in an air atmosphere. Metal oxide semiconductor sensors of the N-type, such as tin oxide, zinc oxide and the like, are used to detect the target gases. The gas detecting devices disclosed in U.S. Pat. Nos. 3,676,820 and 4,457,161 are further examples of devices which detect threshold levels of target gases.

The known gas sensors adsorb the target gases and convert the concentrations of gases into an electrical signal by changing resistivity. The known semiconductor sensors of the thin film type are composed of semiconducting materials, such as metal oxide ceramics, or organic semiconductor materials and others.

With semiconductor sensors the concentration of a combustible or "target" gas is related to the change in the electrical resistance of the semiconductor film. The change in resistance is due to changes of temperature and the presence of reducing gases and solvents. In the presence of reducing gases the concentration of electrons in the surface of the metal oxide film changes due to the adsorption/desorption and reaction of ionic species at the surface of the film. The oxidation/reduction chemical reaction between adsorbed oxygen and the combustible gas yields a product that is desorbed from the surface. Upon removal of the combustible gas from the oxygen-containing atmosphere, the consumed surface-desorbed oxygen is replenished and the resistance of the metal oxide film returns to its original value.

The film surface-adsorbed oxygen will also be affected by the reactive vapor impurities in the ambient air. Water vapor, a common constituent in ambient air, is known to affect the response of a metal oxide film gas sensor in the same manner as a combustible gas. Some other reactive vapors in the air can be those of common solvent contaminants. These are normally referred to as "interference" gases, such as ethanol, methanol, isopropanol, ammonia, benzene, toluene, pentane and hexane.

The total change in the resistance of a metal oxide film sensor arises due to the change in the target combustible gases and all the interference gases that are present in the ambient air being tested. Also, it has been shown that by adding catalytic metals to tin oxide material, the response characteristics of a gas sensor will change at any given operating temperature. Another factor affecting response characteristics is the use of internal binders to hold metal oxide sensing particles in contact with the electrodes and substrate. Internal binders cause an undesireable increase in the response of the sensor to humidity. Insufficient concentration of internal binders leads to mechanical instability throughout the sensing film, causing inaccurate readings and shortened life times.

The multi-gas/multi-sensor system in U.S. Pat. No. 4,542,640 requires that the number of thick film sensors should be greater than or equal to the number of selected gases to be distinguished. Each sensor in the array of sensors should have a response characteristic which differs from the response characteristics of each of the other sensors in its response to at least one of the set of selected gases. This difference may result from changes such as film composition and film gas sensor temperature that can be adjusted in a multi-sensor array to obtain the different responses for each sensor.

The responses of each gas sensor in the above described array are measured for each of the selected gases and the combinations of the selected gases. The measured responses are applied to a system of gas response equations in which each response is substituted in the specific equations and the values of the constants are determined. The equations are then solved for the concentration of the gases in the target gas mixture.

The accuracy of the multi-gas/multi-sensor approach disclosed in U.S. Pat. No. 4,542,640 depends on the extent of the gas response data of all the combinations of the reactive gases in the mixture. For a multi-component gas mixture, as often encountered, the collection of gas sensor data with all the possible combinations of gases can be very time consuming. This limits the collection of data to the single, and some of the important binary combinations. As a result the accuracy in the calculated gas concentrations will then be compromised to the extent of the contribution of those responses that were eliminated. In order to use the multi-gas/multi-thick film sensor system disclosed in U.S. Pat. No. 4,542,640 and maintain the necessary simplicity and accuracy that is demanded of a commercial gas monitoring instrument one must increase the relative gas selectivity from the appropriate choice of film compositions and film temperatures in the array of sensors.

Overall the desired absolute selectivity and accuracy required in the detection of target gases is not achievable with a single approach using the known oxide film gas sensors. For a set of target combustible gases in common ambient background interference, there is a need to use means other than the film composition and temperature to minimize the effect of the interference gases on the combustible gas response of the sensor. Further there is need to address the fact of reaction rate differences between certain target gases such as methane and carbon monoxide and some common "interference" gases, such as ethanol with a tin oxide based film. Overall there is a need to provide a distinct sensor response to different target gases and to minimize the effect on the film resistance response to interference gases.

It is also known, as disclosed in U.S. Pat. Nos. 4,457,161 and 4,481,499, that gas sensors formed from different kinds of metal oxide materials have different gas selectivities to specific gas components of a mixed gas. Therefore there is need to provide a film composition that exhibits favorable catalytic activity with respect to solvents so that the effects of interference from gases other than the target gases are minimized while the sensitivity to target gases is improved. Accordingly an array of thick films that produces the preferred carbon monoxide and methane signals will enhance the accuracy in the calculated concentrations of these target gases.

SUMMARY OF THE INVENTION

In accordance with present invention there is provided apparatus for the selective detection of a gas in ambient air that includes an electrically insulating substrate and a pair of electrodes positioned on said substrate. A gas sensor film is positioned on the substrate in contact with the pair of electrodes. The film has a preselected response characteristic for a selected gas to be detected. Means is provided external to the gas sensor film for securing the film to the substrate in contact with the electrodes. Filter means integral with the gas sensor film minimized the effect of interference gases on the response of the film for the gas to be detected such that combustion of the interference gases, occurs on the outer layer of the film away from the electrodes. Means is provided for heating the gas sensor film to a preselected elevated temperature on the substrate.

Further in accordance with the present invention there is provided a selective gas sensing film that includes a heating element. A substrate is positioned on the heating element. A pair of electrodes are positioned in spaced relation on the substrate. A metal oxide film is positioned on the substrate in contact with the pair of electrodes. A non-porous glass layer surrounding the metal oxide film anchors the metal oxide film to said substrate and said pair of electrodes.

Accordingly, the principal object of the present invention is to provide a metal oxide base thick film gas sensor that is selective in the detection and measurement of the concentration of a target gas in ambient air.

Another object of the present invention is to provide a catalytically active tin oxide based composition for thick films assembled in an array of sensors for the selective detection and measurement of target gases.

An additional object of the present invention is to provide a gas response having a preselected degree of sensitivity to a target gas while maintaining low non-target gas interference, low power consumption, low water response, and response stability.

These and other objects of the present invention will be more completely disclosed and described in the following specification and accompanying claims.

DESCRIPTION OF THE PREFERRED EMBODIMENTS

Figure 1:
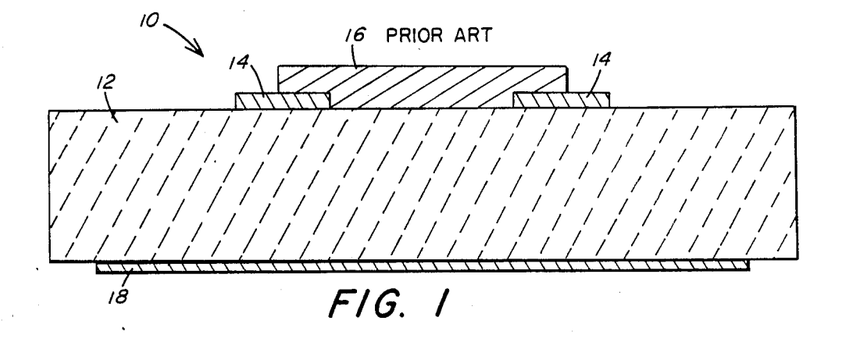
FIG. 1 is a schematic cross-sectional view of a prior art embodiment of a metal oxide thick film gas sensor.

Referring to FIG. 1 there is illustrated a conventional gas sensor generally designated by the numeral 10 for determining the presence and concentrations of selected polluting, toxic, and combustible gases, such as carbon monoxide, methane, hydrogen sulfide, alcohol vapors, and many other gases. Conventionally a plurality of sensors 10 are grouped in an array as disclosed in U.S. Pat. No. 4,542,640. The number of individual sensors 10 in the array is greater than or equal to the number of selected gases to be distinguished. Each sensor 10 of the array has a response characteristic which differs from the response characteristics of each of the other sensors in the array to at least one of the set of selected gases.

A pair of electrodes 14 are supported by the substrate 12 and are in contact with a N-type semiconductor material 16, such as a film layer of stannic oxide of a preselected thickness. Preferably the electrodes 14 are spaced a preselected distance from one another. A heater 18, generally a metallic film of a preselected resistance, heats the semiconductor material 16 to an operating temperature, for example between 400° C. to 600° C. The electrodes 14 are connected to an electrical resistance measuring device, such as an ohmmeter (not shown). When a reducing gas is adsorbed by the semiconductor material 16, a decrease in the electrical resistance of material 16 is measured.

As further disclosed in U.S. Pat. No. 4,542,640 signal processing methods which rely on a gas sensor's differing relative sensitivities to different gases are used to compute the constituent gas concentration. For example, an array of precalibrated semiconductor gas sensors 10 are coupled to a processing unit which measures sensor resistances and transforms signals representing the resistances into signals representing individual gas concentrations. A central processing unit receives the sensor signals from the array of gas sensors 10. The processor can then be used to provide a digital readout of gas concentrations or transmit the values of the gas concentrations by electrical means for other forms of display. The processor can also be used to provide an indication such as an alarm signal whenever a particular gas concentration attains a predetermined value or whenever gas concentrations or combinations of gas concentrations exceed threshold values.

Generally the sensor response is an indication of the resistance change that occurs when the gas sensor 10 comes in contact with a reducing gas or combustible solvent. The response is appropriately reported as a measurement of the resistance of the sensing material in clean "baseline" air divided by the resistance of the sensing material in the presence of a reducing gas.

The electrical resistivity of the sensing material 16 is dependent upon the amount of oxygen that is adsorbed on the exposed surfaces. The amount of adsorbed oxygen depends on the oxygen partial pressure in the intergranular spaces and on the partial pressures of any combustible gases that react with adsorbed oxygen. If a gas reacts readily with the adsorbed oxygen, then the presence of that gas will result in a decrease in the amount of adsorbed oxygen resulting in a decrease in the electrical resistivity.

The selectivity of the gas sensor 10 is determined by the catalytic nature of the sensing material and the electrode material interface.

The selectivity of sensor 10 can be improved, for more thermodynamically stable target gases, with respect to less thermodynamically stable interference gases. This is accomplished by extending the sensing material in all directions, such that distance to the sensitive region near the electrodes by any given path is sufficient to pyrolyze a large fraction of the interference gases away from the electrode region, while pyrolyzing only a fraction of the target gas away from the electrode region. The appropriate material thickness, which is practically limited for this simple structure by thermal stresses applied to the extended material, depends on many variables such as, catalytic activity, an effective surface area of the material, plus the operating temperature of the sensor, and the gases in question. In practice the appropriate thickness is determined empirically.

Figure 2:
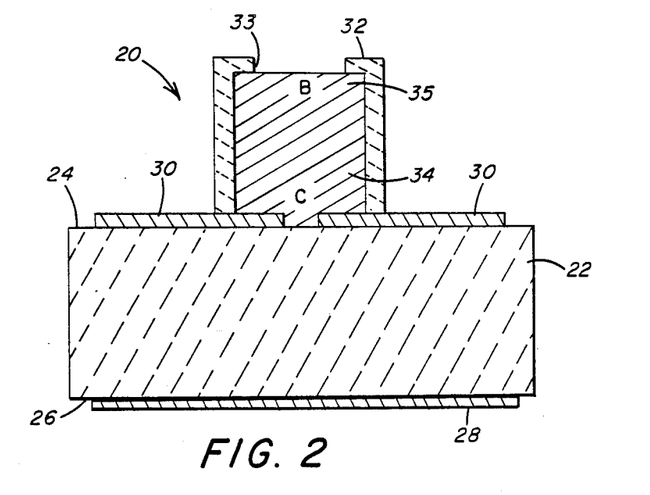
FIG. 2 is a schematic cross-sectional view of a thick film gas sensor of the present invention, illustrating a substrate supporting a pair of electrodes in contact with a metal oxide gas sensing film anchored to the substrate by a non-porous glass ring layer.

Referring to FIG. 2 there is illustrated in accordance with the present invention a gas sensor generally designated by the numeral 20 that includes an electrically insulating substrate 22, such as alumina, having an upper surface 24 and a lower surface 26 to which is secured a film heater 28, such as a platinum film heater 28. A pair of electrodes 30 are spaced apart horizontally on the substrate upper surface 24.

A metal oxide film or layer 34 extends upwardly from the substrate surface 24 and the electrodes 30. A nonporous glass layer 32 anchors the film 34 to the substrate surface 24 and electrodes 30. The layer 32 is a ring-like structure which surrounds the film 34 but includes an opening 33 for exposing a selected portion of the film 34 to the ambient air conditions. The layer 32 includes electrical insulating material.

The glass layer 32 overcomes the adverse effects of using internal binders to hold together the metal oxide powder particles. The glass layer 32 imparts superior mechanical strength to the underlying structure. This increased strength allows thicker metal oxide films to be made than heretobefore possible by thick film fabrication methods, such as by screen printing.

Figure 2A:
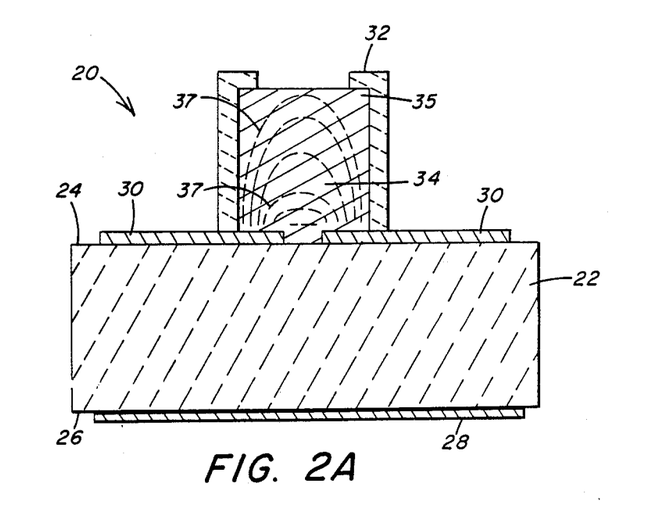
FIG. 2A is a view similar to FIG. 2, illustrating the relative magnitude of the current field throughout the gas sensing film.

The glass layer 32 is non-porous so that all the gases must enter the opening 33 and pass through the entire thickness of the metal oxide film 34 from point B near the exposed outer surface of the film 34 to point C where the electric current is largest, as shown in FIG. 2A by the conductive path lines 37. By increasing the thickness of the metal oxide film, the response can be made much less sensitive to an interference gas such as ethanol which is more readily combusted. In this respect the sensing material adjacent point B serves as a filter layer 35 which is integral with the gas sensing layer 34.

A less chemically stable gas, such as ethanol, is combusted primarily near the outer surface point B and does not penetrate appreciably to point C, where combustion of ethanol would produce a large measured change in resistance. Consequently, the response to a target gas such as methane, which is more chemically stable, will not be reduced as much because the methane is combusted more uniformly throughout the metal oxide layer 34. Thus by controlling the diffusion path of the interference and the non-target gases through the layer 34, it is possible to reduce their concentrations so that the less reactive target gases will generate a relatively larger signal. The optimum thickness of a filter for a specific target gas and sensor is determined empirically.

The filtering effect of the metal oxide layer 34 at point B in FIG. 2 can be further exploited by the addition of a porous electrically insulating layer, as will be explained later in greater detail with reference to FIGS. 4 and 5. The electrical current paths do not extend beyond the insulating layer. Combustion of interference gases, such as ethanol, in the filter layer 35 do not produce measurable electrical signals. If the filter layer 35 is composed of an electrically insulating catalytic material, then a porous electrically insulating layer below the filter layer 35 is not needed.

Figure 3:
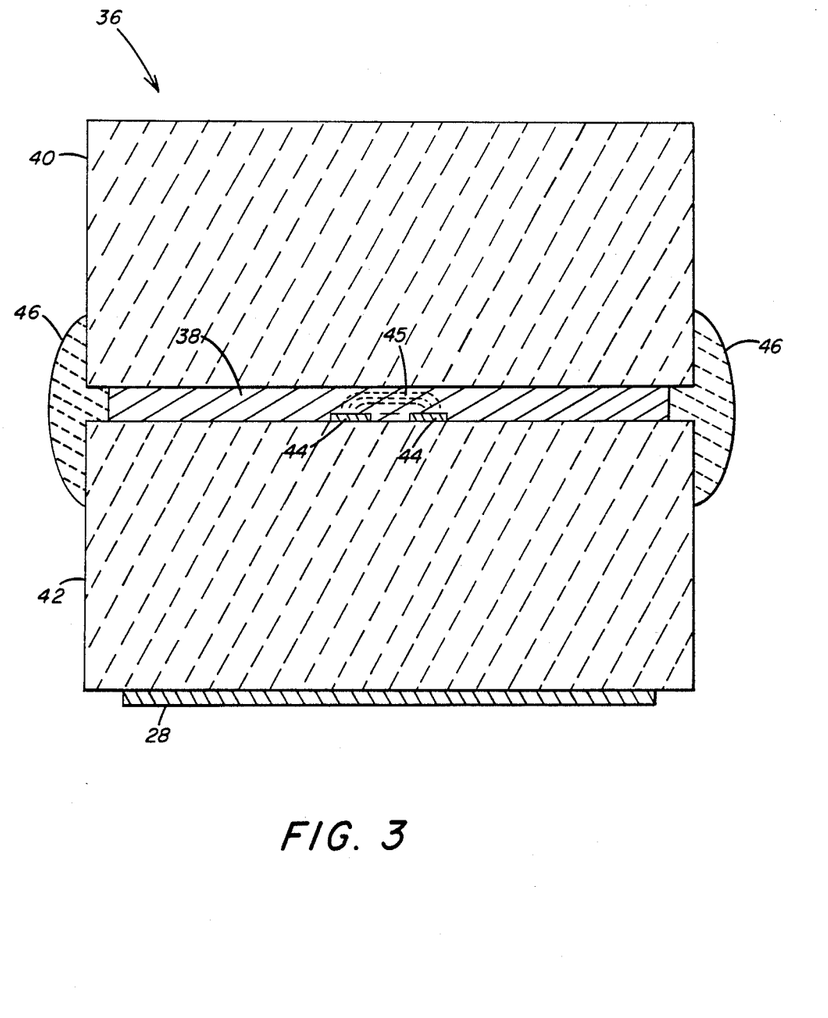
FIG. 3 is a schematic cross-sectional view of another embodiment of a gas sensing film, illustrating a pair of electrodes embedded in a metal oxide film sandwiched between upper and lower alumina substrates which are connected by a porous glass layer.

Now referring to FIG. 3 there is illustrated a gas sensor generally designated by the numeral 36 having the characteristics of a substantially increased film thickness without having to sacrifice mechanical stability of the structure. This embodiment can be characterized as "a sandwich" sensor. A gas sensing layer 38 of a metal oxide film is sandwiched between an upper alumina substrate 40 and a lower alumina substrate 42. A pair of electrodes 44 are buried in the gas sensing layer 38 on the upper surface of the lower substrate 42. The lines 45 designate the conductive paths between the electrodes 44. The upper substrate 40 serves as a gas blocking element to inhibit interference gases from diffusing from the top and has the effect of increasing the thickness of sensing layer 38. With this arrangement an extra long filter length is available. A peripheral glass layer 46 bonds the upper substrate to the lower substrate around the gas sensing layer 38.

Figure 4:
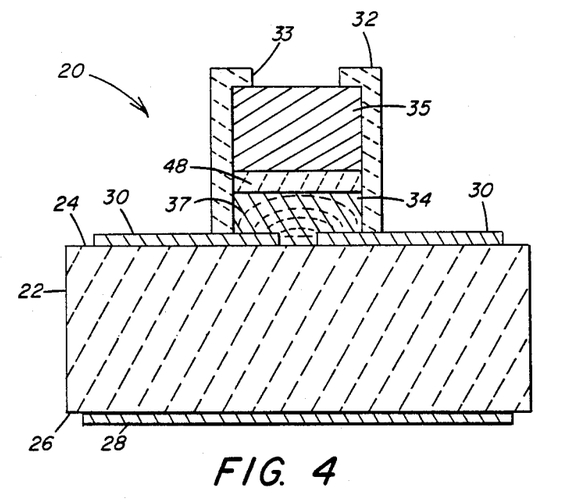
FIG. 4 is a schematic cross-sectional view of a thick film gas sensor similar to FIG. 2, illustrating conduction paths through a metal oxide film covered by a porous glass layer.
Figure 5:
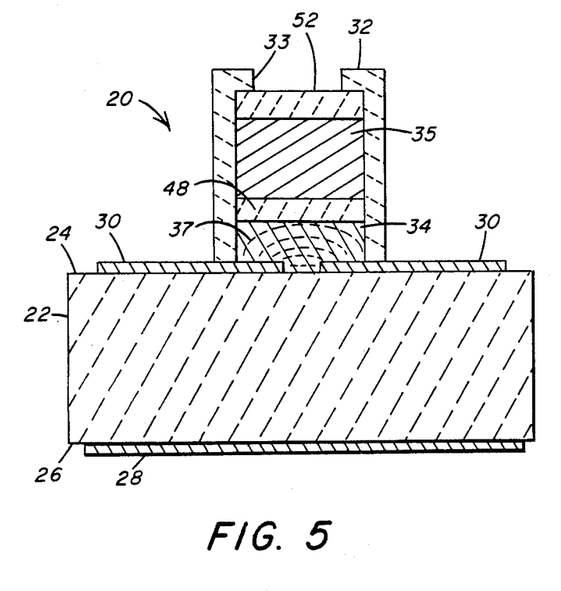
FIG. 5 is a schematic cross-sectional view similar to FIG. 4, illustrating an additional porous, electrically insulating layer.

Now referring to FIGS. 4 and 5 there are illustrated further embodiments of the present invention in which like numerals in FIGS. 4 and 5 refer to like parts in FIG. 2. In FIG. 4 a porous electrical insulating layer 48 extends through the metal oxide film 34. The layer 48 serves to confine the current paths in close proximity to the electrodes 30. Accordingly, the filter layer 35 is positioned above the insulating layer 48. If the filter layer 35 includes electrically insulating catalytic material, then the porous electrically insulating layer 48 is not needed. With the insulating layer 48 the metal oxide film sensing material in the filter layer 35 combusts the interference gases resulting in a materials resistance change but the change is not measured by the electrodes 30.

FIG. 5 illustrates a porous sintered glass layer 52 positioned atop the filter layer 35 beneath the non-porous glass layer 32. The glass layer 52 provides increased mechanical stability to the powder materials comprising the filter layer 35 and the metal oxide film 34 on the substrate 22. Further, by using the electrically insulating layer 48, a variety of conductive catalytic metal oxide semiconductor materials for filter layer 35 can be used with or without metal catalysts. Also, by using a non-conductive catalyst for the filter layer 35 the need for the electrically insulating layer 48 is obviated. In this manner the appropriate materials are chosen for the desired filtering approach.

Platinum or palladium coated gas sensing metal oxide powders with special preparation characteristics have been found to be suitable catalysts for the filter layer 35. Preferably the tin oxide sensing layers 34 are impregnated with platinum or palladium chlorine-free precursors. A suitable source are tetramine nitrates of platinum or palladium. These salts are soluble in water and convenient to use for the impregnation of the powder.

In one example the appropriate amounts of salts for 2 wt % of either platinum or palladium in tin oxide were weighed and dissolved in small amounts of distilled water. Then tin oxide powder was sieved to a particle size equal to or less than 43 microns and added to a quartz boat containing the above solution. The powder was completely slurried by the addition of a volatile liquid, such as ethanol. The mixed slurry was predried under a chemical hood, crushed, and remixed in the same boat. The powder was then heated in a resistance type tubular furnace in flowing air. The mixture was first heated to 450° C. in about 1.5 hours and then maintained at 450° C. for 5 hours. The furnace was then cooled and the powder mixture was ground and sieved to a particle size equal to or less than 43 microns before it was used to make the sensor films. Platinum or palladium containing tin oxide powders prepared as above are also suitable as single sensing layer materials for selective methane sensors.

Another improved formulation for the tin oxide sensing layer includes the addition of small amounts of gold to the tin oxide powder. The addition of gold to the tin oxide powder is particularly adaptable where the films are used with gold electrodes. A suitable source for the gold is AuCl₃. Gold electrodes provide higher carbon monoxide responses than those obtained with platinum electrodes under comparable gas testing conditions. Thus a gold-doped tin oxide powder has been found to further enhance the carbon monoxide response relative to that for methane when used with gold electrodes.

In one example gold in the amount of 0.1-0.2 wt % was used in the tin oxide powder mixture. The appropriate amount of gold chloride was dissolved in ethanol. Tin oxide powder having a particle size of up to 43 microns was added to form a slurry in a quartz boat. This mixed slurry was predried under a chemical hood. The resultant "cake" was crushed and mixed inside the boat and then fired in flowing air to 700° C. The boat was brought to 700° C. within half an hour and then held at 700° C. for one hour. The powder mixture was then cooled, ground and sieved to a particle size equal to or less than 43 microns for making a gold-doped tin oxide powder film.

It has also been found that a nonconductive filter layer 35 formed of catalytically doped alumina and a crystallizable glass dielectric provides an exclusive methane response in the sensing layer 34. An example of nonconductive filter layer 35 includes two parts of 5% platinum or palladium doped alumina mixed with one part glass. This film composition when used as the filtering layer 35 provides an increased, exclusive response for methane, particularly when the sensing layer 34 is formed of a gold-doped tin oxide powder and the electrodes 30 are platinum. The glass is added in paste form to provide the filter layer 35 with mechanical integrity.

To increase the carbon monoxide to methane ratio for an operating temperature of the gas sensing layer 34 of no greater than 400° C., the tin oxide powder is doped with antimony. The incorporation of an internal dopant like antimony in the structure of tin oxide sensing film layer lowers the resistance of the layer to within a conveniently measured range to obtain a response where the film is operated at a temperature between 350° C. to 550° C., and preferably about 400° C. By lowering the response temperature it is possible to lower the film heater power requirements.

The antimony doped film composition is prepared first by dissolving potassium antimony tartrate in dilute nitric acid and then added to an acidic solution of tin. The metastannic acid precipitates out where the antimony is carried onto the precipitate. Thereafter, the precipitate is heated in air to a temperature greater than 850° C. The antimony doped tin oxide has the formulation $Sn_{1-x}Sb_xO_2$. Further heating to above 1000° C. ensures a stable antimony doped tin oxide powder.

Prior to heating the precipitate at 850° C. it is preferably predried in a vacuum oven at about 100° C. This provides a hydrated form of the metastannic acid powder in view of the fact that the water has been partially expelled. Also before being fired at the elevated temperature to obtain the oxide form, the metastannic acid powder is easily ground to a particle size equal to or less than 45 microns. Most preferably the metastannic acid powder after predrying in the vacuum oven at 100° C. is ground and sieved before it is fired at higher temperatures. The eliminates the step of grinding and sieving after the combustion stage. If the mixture is fired first, it becomes hard, increasing the time and difficulty of the grinding process.

This method is preparing an antimony doped tin oxide powder is also preferred over those methods which require the use of chlorides of antimony and their addition to an ammonium hydroxide solutions as disclosed in U.S. Pat. No. 4,614,669. By using a potassium antimony tartrate as a solid which is conveniently added to the solution eliminates the precautions that are required in the use of chloride liquids. One advantage achieved by the antimony doping is that the measurable range of the sensing film resistance can be selected by the addition of trace amounts of antimony in the tin oxide sensing layer.

Further in accordance with the present invention the use of gold coated powders also provides additional increase in the carbon monoxide response and high carbon monoxide/methane ratios at operating temperatures equal to or less than 400° C. The use of the gold doped tin oxide is combined with the use of gold electrodes. By operating the sensing layer 34 at 400° C. with a gold doped $Sn_{1-x}Sb_xO_2$ formulation provides a response equation for high carbon monoxide signals. The methane response equation is also provided with the platinum or palladium doped $Sn_{1-x}Sb_xO_2$ at 400° C. in the same manner described for tin oxide films without the antimony dopant. A comparable methane and carbon monoxide response is also obtained at only 400° C. with only $Sn_{1-x}Sb_xO_2$.

Preferably the percentage by weight of platinum and palladium in tin oxide or its antimony containing variation ($Sn_{1-x}Sb_xO_2$) is in the range between 0.5 wt %-5 wt %. The range for gold doping in the tin oxide composition is in the range between 0.1 wt %-0.3 wt %. In the above formulation for antimony doped tin oxide, x is between 0.005 and 0.03.

The filter layer 35 may be a conductive film (tin oxide based) or a nonconductive film (ceramic based). The conductive film is stannic oxide powder coated by platinum or palladium catalysts. Most preferably the filter layer 35 is prepared from chlorine free precursor compounds. The result is a platinum or palladium coated powders of $SnO_2$ or its variant antimony doped formulation $Sn_{1-x}Sb_xO_2$ using precursors, such as tetramine nitrate salts in the formulation or Conductive filter layers of this type have been found to demonstrate superior catalytic activity for methane sensitivity.

Similarly nonconductive gas filter layers are prepared using the same approach for preparation of the conductive gas filter layer. The nonconductive film is typically alumina, coated with a platinum or palladium catalyst.

The above described conductive films have a given methane selectivity when used alone in the form of single gas sensing film layer 34. A methane selective response is obtained at temperatures close to 400° C. in contrast to known film-type detection systems as disclosed in U.S. Pat. No. 3,625,756 which give a methane selective response at about 550° C. without the benefit of impregnated platinum or palladium powders in accordance with the present invention.

Filtering of interface gases in a metal oxide gas sensor can also be accomplished by physical means, such as incorporation of a small solvent vapor getter bed material which is positioned in a cool region adjacent to the gas sensor unit and through which the gases must pass. A suitable vapor getter is activated charcoal for gettering common vapors, such as ammonia, benzine, toluene, gasoline and the like. The target gases, such as methane and carbon monoxide, would not have any absorption affinity to the vapor-getter material.

The getter material has appreciable saturation capacity for contaminant vapors with a life expectancy of several months to a year before replacement. The affect of the vapor-getter is to increase the signal to noise ratio. A solvent vapor filter material allows only the target combustible gases, such as carbon monoxide and methane and also water vapor, to come in contact with the surface of the films. The use of such activated charcoal filter bed material has not heretobefore been used in gas sensing film devices of the present invention.

Further, in accordance with the present invention the above described gas sensors are most preferably used for the simultaneous detection of a plurality of target gases. These sensors can be arranged in an array on a singly heated substrate, or on individually heated substrates in a manner that facilitates the response for each sensor to provide a selective gas detection. The use of nonselective metal oxide sensors to provide selective gas detection is based on the principle that the resistance of the sensor depends on the concentration of each of the target gases, $G_i$, and a set of coefficients $C_1$ as represented by the following formula:

$$R = F(G_1 \ldots G_n, C_i \ldots C_M)$$

where the number of sensors, N, is greater than or equal to the number of target gases, n.

Each of the selective sensors has a distinct response with respect to the other sensors. The coefficients $C_i$ in the response equation for each of the sensors is determined. By use of a microprocessor the gas concentrations $G_i$ are determined given the resistance of each sensor, $R_s$, and the coefficients, $C_i$.

The appropriate sensors for use in the array must first be selected. The sensitivity, $S_{sg}$, for each sensor with respect to each gas is represented by the following formula:

$$S_{sg} = F_s(G_1 = 0, G_2 = 0 \ldots G_n = 0)/F_s(G_g = G_t)$$

where $F_s(G_1 = 0, G_2 = 0 \ldots G_n = 0)$ represents the clean air resistance of the sensor and $F_s(G_g = G_t)$ represents the resistance of the sensor when exposed to a preset level of one of the target gases. Sensors must be selected with values for S that are enhanced for one or more of the target gases. In the case where three sensors are used to detect two gases, a first sensor is partially selective to a first gas, a second sensor is partially selective to a second gas, and a third sensor is equally sensitive to both gases.

In the case of detecting three gases four sensors are used and a number of choices are available. The first three sensors are partially selective to a different gas and the fourth sensor is equally sensitive to all gases. In a second case the first three sensors are selective to two of the three gases and the fourth is selective to all the gases. In another case sensors one and four are partially selective to one gas each and sensors two and three are sensitive to two gases each. There are many combinations that will yield the desired result of having four sensors with distinct responses. So in the general case of n gases and N sensors, the number of possible distinct sensors grows rapidly with the number of gases.

In accordance with the gas sensors of the present invention, desired partial selectivity has been obtained by using the appropriately doped metal oxide sensor material. The insensitivity to noise gases has been obtained using the above described filter layers to combust these gases. The stability of the sensor has been obtained by choosing and correctly applying the appropriate catalysts and glass layers.

The coefficients used in the above model equation are determined for each sensor by a calibration procedure which subjects the sensor to a number of test atmospheres of known composition. The resistance of the sensor corresponding to each gas mixture, along with the known gas concentrations, are provided as input data to a least-squares fitting routine which calculates the coefficients in the sensor response equations.

The test air to which the sensors are subjected must contain controlled concentrations of each target gas and be free of any other gases that might affect the sensor resistance. These conditions must be maintained for a sufficient length of time to allow the gas sensors to achieve equilibrium. Because the gas sensors consume the target gases and generate other gases to which the sensors might respond, the test air must be continuously replaced to ensure that the target gas concentrations remain constant and that the concentrations of combustion by-products remain small.

The concentration of each target gas must be delivered over a range comparable to the intended range of detection. Moreover, because of the non-linear nature of the response model at least three distinct test concentrations must be used for each target gas. If any of the nonselective sensors has a response to a particular gas that is either suppressed or enhanced by the presence of one of the other target gases, then it is necessary to include also test air mixtures containing both gases simultaneously. The coefficients are determined by minimizing the quantity:

$$X^2 = (R^2_i - F^2_i)$$

where $R_i$ is the measured resistance for sensor i and $F_i$ is the model equation for sensor i.

In one example three sensors were utilized to detect methane and carbon monoxide. One sensor was partially selective to methane, a second sensor partially selective to carbon monoxide and a third sensor with similar sensitivity to both gases. The sensors were mounted on a wand connected to a processor control circuit through a cable. The processor control circuit controls the operating temperature of each sensor, measures the resistance of each sensor, and passes this to the fitting algorithm where the resulting gas concentrations are calculated. The resulting values for the individual concentrations are digitally displayed.

The processor is also serially interfaced with a calibration/test computer. The devices are placed in a calibration housing and the calibration computer sets the gas concentration delivered to the housing. After an appropriate period of time the calibration/test computer actuates the processor control board to read the resistances passed through the serial interface. This data is then used by the calibration/test computer to determine the coefficients. The coefficients are then entered into the processor control board memory to calculate the respective gas concentrations.

In one example of the present invention, a gas detection system includes an array of three sensors for the detection of methane and carbon monoxide. The response of each of the three sensors is determined by the selection of the appropriate metal oxide powders, use of filter layers, and control of the thickness of the sensor film and filter layer. Thus the array of sensor devices contains a sensor that is partially selective to methane, a sensor that is partially selective to carbon monoxide, and a sensor that has similar sensitivity to both gases. In addition these sensors are relatively insensitive to interfering gases, such as ethanol or water vapor.

In application the array of sensor devices are electrically connected to a data acquisition/control unit which is, in turn, connected to a processor unit. The processor unit performs two basic functions. First it sets and controls the temperature of the sensors in a manner that allows the sensor temperature to remain constant in the presence of fluctuating ambient conditions. Precise temperature control provides stable sensor operation. A temperature controller applies the known temperature/resistance relationship for platinum to the heater on the substrate. In this manner the heater functions as a thermometer for the purpose of controlling temperature.

Secondly the processor calculates the gas concentrations based on the electrical resistance response of the individual sensors in the array. The algorithm used for the gas detection analysis involves solving nonlinear equations in a process which converges to the desired result independent of the starting point. The algorithm automatically adjusts the manner in which the step, size and direction are chosen based on the convergence criteria of the previous iteration. The above algorithm is self adjusting in a manner that will always converge at an optimum rate independent of the starting point.

Figure 6:
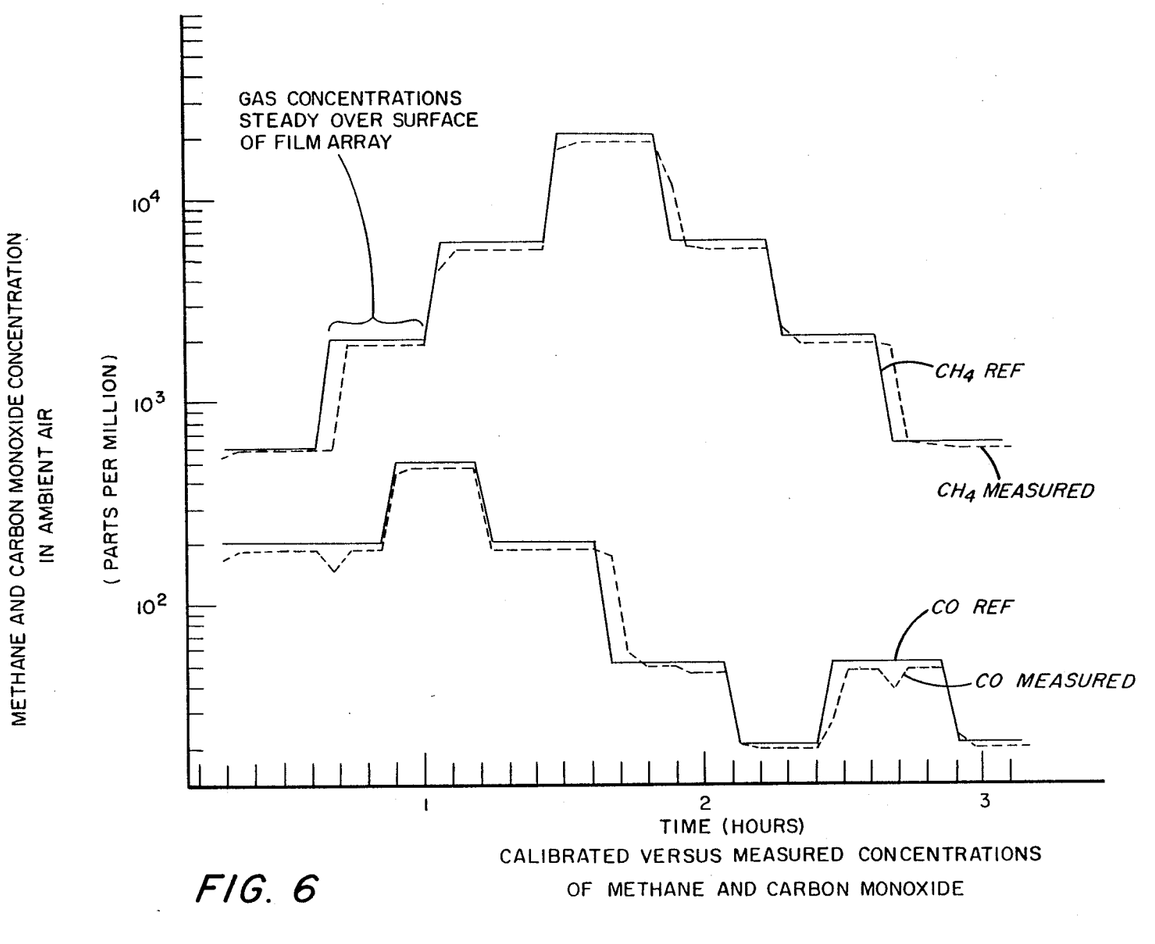
FIG. 6 is a diagrammatic representation of measured concentrations of methane and carbon monoxide in accordance with the present invention compared with actual concentrations of the gases.

In a test of the present invention for a selection of gas concentrations, as shown in FIG. 6, the gas concentrations in ambient air were measured by the sensing devices. The measured values were compared with the calibrated values of methane and carbon monoxide. For a wide range of values the sensing devices demonstrated good accuracy over a wide range of gas concentrations with very little interference between the two gases.

According to the provisions of the patent statutes we have explained the principle, preferred construction and mode of operation of our invention and have illustrated and described what we now consider to represent its best embodiment. However, it should be understood that, within the scope of the appended claims the invention may be practiced otherwise than as specifically illustrated and described.

We claim:

1. Apparatus for the selective detection of a target gas in ambient air comprising,
   an electrically insulating substrate,
   a pair of electrodes positioned on said substrate,
   a gas sensor film positioned on said substrate in contact with said pair of electrodes,
   said film having a preselected response characteristic for a selected gas to be detected,
   catalytic combustion filter means integral with said gas sensor film for minimizing the effect of interference gases that are less thermochemically stable than the target gases on the response of said film for the gas to be detected by promoting combustion of interference gases on the outer layer of said film away from said electrodes, and
   means for heating said gas sensor film to a preselected elevated temperature on said substrate.

2. Apparatus as set forth in claim 1 which includes,
   a porous electrically insulating layer positioned between said gas sensor film and said filter means for preventing detection of a change in resistance due to combustion of the interference gases.

3. Apparatus as set forth in claim 1 which,
   said gas sensor film includes tin oxide with a preselected amount of antimony as an internal dopant, and
   said antimony being added to said tin oxide material in a preselected amount to adjust the resistance of said film within a preselected resistance range and operation of said gas film sensor at a preselected temperature.

4. Apparatus as set forth in claim 1 in which,
   said means for maintaining said gas sensor film at a fixed temperature in the range between about 350° C. to 600° C.

5. Apparatus as set forth in claim 1 which includes,
   an array of said gas sensor films each positioned on an individual one of said substrates, and
   means for heating each gas sensor film to a different temperature for selectively detecting desired target gases by said array.

6. Apparatus as set forth in claim 1 which includes,
   a low temperature selective solvent vapor filter material positioned adjacent said gas sensor film for limiting access of said gas to be detected by said gas sensor film only through said solvent vapor filter material.

7. Apparatus as set forth in claim 1 in which,
   said means for securing said film to said substrate includes a non-porous glass layer surrounding said film and defining a diffusion path for the flow of the gas to be detected to said gas sensor film.

8. Apparatus as set forth in claim 1 in which,
   said gas film sensor includes tin oxide doped with a catalyst selected from the group consisting of platinum and palladium in the range between about 0.5 wt %–5 wt %.

9. Apparatus as set forth in claim 1 in which,
   said gas film sensor includes tin oxide doped with gold in the amount of 0.1 wt %–0.3 wt %.

10. Apparatus as set forth in claim 1 in which,
    said gas sensor film has the formulation $Sn_{1-x}Sb_xO_2$ doped with gold in the amount 0.1 wt %–0.3 wt % where x has a value between 0.005 and 0.03.

11. Apparatus as set forth in claim 1 in which said gas sensor film includes,
   means external to said gas sensor film for securing said film to said substrate in contact with said pair of electrodes.

12. Apparatus as set forth in claim 11 in which,
   said means for securing said film to said substrate includes a non-porous glass layer surrounding said film and defining a diffusion path for the flow of the gas to be detected to said gas sensor film.

13. Apparatus as set forth in claim 1 in which said gas sensor film includes,
   a first layer fabricated of a gas sensing metal oxide and a second layer fabricated of a conductive catalyst layer, said first layer being in contact with said electrode,
   said first layer having a resistance determined by the composition thereof, and
   said second layer serving as a composition filter layer for inducing combustion on said outer layer of said respective film of the interference gases away from said first layer.

14. Apparatus as set forth in claim 13 in which,
   said second layer of said gas sensor film includes a catalyst for increasing the rate of combustion of the interference gas on the outer layer and thereby enhance the relative sensitivity of the first layer to a preselected target gas.

15. Apparatus as set forth in claim 14 in which,
   said catalyst is selected from the group consisting of platinum, palladium, and gold.

16. A selective gas sensing film comprising,
   a heating element,
   a substrate positioned on said heating element,
   a pair of electrodes positioned in spaced relation on said substrate,
   a metal oxide film positioned on said substrate in contact with said pair of electrodes, and
   a non-porous glass layer surrounding said metal oxide film to anchor said metal oxide film to said substrate and to said pair of electrodes.

17. A selective gas sensing film as set forth in claim 16 in which,
   said non-porous layer is a gas blocking ring electrically insulated from said metal oxide film, and
   said ring including an opening for restricting ambient gas diffusion to said metal oxide film.

18. A selective gas sensing film as set forth in claim 16 which includes,
   a catalytic filter layer positioned above said metal oxide film for combusting interference gases to prevent diffusion thereof into contact with said metal oxide film for enhancing the selectivity of said metal oxide film to a specific target gas.

19. A selective gas sensing film as set forth in claim 16 which includes,
   a tin oxide based conductive film positioned in surrounding relation with said metal oxide film between said glass layer and said metal oxide film, and
   said tin oxide based conductive film having a preselected composition for enhancing the combustion of interference gases substantially removed from said metal oxide film to filter out the interference gases and increase the relative sensitivity of said metal oxide film of one preselected gas to be detected in relation to other gases to which said metal oxide film is exposed.

20. A selective gas sensing film as set forth in claim 16 which includes,
   a gas filtering film separating said glass layer from said metal oxide film, and
   said gas filtering film having a preselected composition for enhancing the combustion of interference gases substantially removed from said metal oxide film and thereby filter out the interference gases and increase the sensitivity of said metal oxide film to a preselected target gas to be detected in relation to other gases.

21. A selective gas sensing film as set forth in claim 20 which includes,
   a porous sintered layer positioned within said nonporous layer above said gas filtering film for enhancing the mechanical stability of said metal oxide film.

22. A selective gas sensing film as set forth in claim 20 in which,
   said gas filtering film includes a non-conductive catalyst.

23. A selective gas sensing film as set forth in claim 20 in which said gas filtering film includes,
   a ceramic material doped with a preselected material selected from the group consisting essentially of platinum and palladium.

* * * * *